(12) United States Patent
Bushnell et al.

(10) Patent No.: US 6,676,408 B1
(45) Date of Patent: Jan. 13, 2004

(54) DIRECT PNEUMATIC PISTON DRIVEN IMPRESSION MATERIAL DISPENSING SYSTEM

(75) Inventors: Raymond Bushnell, Beaver Creek, OR (US); Sheri Gillett, Salem, OR (US); Andras Hites, Point Richmond, CA (US); George Hites, Pleasanton, CA (US)

(73) Assignee: MicroDental Laboratories, Inc., Dublin, CA (US)

( * ) Notice: Subject to any disclaimer, the term of this patent is extended or adjusted under 35 U.S.C. 154(b) by 0 days.

(21) Appl. No.: 09/958,528

(22) PCT Filed: May 4, 2000

(86) PCT No.: PCT/US00/12144

§ 371 (c)(1),
(2), (4) Date: Jun. 20, 2002

(87) PCT Pub. No.: WO00/66027

PCT Pub. Date: Nov. 9, 2000

Related U.S. Application Data

(60) Provisional application No. 60/132,517, filed on May 4, 1999.

(51) Int. Cl.[7] .............................. A61C 9/00; B67D 5/00
(52) U.S. Cl. .............................. 433/36; 433/90; 222/638
(58) Field of Search ............................ 433/36, 37, 80, 433/89, 90, 226; 222/263, 333, 334, 638

(56) References Cited

U.S. PATENT DOCUMENTS

| | | | | |
|---|---|---|---|---|
| 4,704,088 A | * | 11/1987 | Newman | 433/81 |
| 4,991,755 A | * | 2/1991 | Grusmark | 222/638 |
| 5,370,533 A | * | 12/1994 | Bushnell | 433/36 |
| 5,722,829 A | * | 3/1998 | Wilcox et al. | 433/90 |
| 5,816,445 A | * | 10/1998 | Gardos et al. | 222/1 |

* cited by examiner

Primary Examiner—Todd E. Manahan
(74) Attorney, Agent, or Firm—Dergosits & Noah LLP

(57) ABSTRACT

A viscous material dispensing system 100 utilizes pressurized gas directed to one end of a piston 109 and cylinder 103 assembly to extrude impression material 128, 129 from a dispenser 121 through a tube 133 into a dental tray 135 which hardens to form a mold of the patient's mouth. The movement of the piston 109 is controlled by switches 147, 149 which control gas valves 143, 145 which direct the pressurized gas to either side of the piston 109. A timer 141 is built into the material dispensing system to monitor the working time and the set time of the impression material 128, 129 after it has been injected into the dental tray 135.

20 Claims, 4 Drawing Sheets

US 6,676,408 B1

DIRECT PNEUMATIC PISTON DRIVEN IMPRESSION MATERIAL DISPENSING SYSTEM

This application claims the benefit of Provisional application Ser. No. 60/132,517, filed May 4, 1999.

FIELD OF INVENTION

The present invention is in the field of dental impression material handling systems.

BACKGROUND OF THE INVENTION

Dental reconstruction and cosmetic surgery often required the repair of human teeth. In order to help facilitate this repair, models of a patient's teeth and gums are made so that accurate repair pieces can be made. The models of teeth and gums are typically made by making a mold of the patient's mouth. A tray having a "U" shaped cross section is connected via tubes to an impression material injection system. The tray is placed in the patient's mouth and impression material is injected through the tube into the tray until the teeth and gums are surrounded. After the impression material hardens the tray is removed from the patient's mouth forming a mold of the patient's mouth. The hardened mold is then used to make a positive of the patient's mouth.

The impression material is typically stored as two separate flowable components which are mixed together just before being injected into the dental tray. After mixing, the impression material has a working time during which the mixture remains a flowable material and can be manipulated and a set time after which the impression material polymerizes or rubberizes. The time after the impression material is mixed is monitored so that adjustments to the tray and impression material are not made after the working time has expired. The impression material polymerizes or rubberizes and after the set time has elapsed the tray can be removed from the patient's mouth.

The impression material may be a silicone or any other suitable material. The working time, set time and viscosity are characteristics of the impression material that are specified in literature supplied by the manufacturer. The working time is typically 1.5 to 2.5 minutes and the set time is 2.25 to 5 minutes. Dental impression material is currently available in either cartridge or pouch dispensers of various standard volumes, including: 25, 50 and 75 milliliters.

A number of systems have been developed for handling impression material. U.S. Pat. No. 4,472,141 discloses several mechanical devices including: levers, ratchets and gears/screws which drive a plunger into a barrel which may contain a dental impression material. The use of these mechanical devices applied to dental impression applications is problematic because the flow of impression material is a function of the force exerted by the operator. It may be difficult for the operator to regulate the mechanical device force so that an even flow of material is produced.

Electric motors may be used to extrude impression material from a dispenser. Westone Laboratories and Dispensing Technologies International sell devices having an electric motor which rotates a gear mechanism which drives a piston into the dispenser to extrude impression material. A manual switch controls the motor and movement of the piston and the flow of impression material from the dispenser.

Pressurized gas systems have also been developed for the extrusion of dental impression material. U.S. Pat. No. 5,370,533 discloses a mechanism which uses pressurized gas to move a piston and drive a rod into a dispenser which extrudes impression material through a tube to a dental tray. Pressurized gas systems can be large heavy floor mounted systems which are connected to the dental tray with a long tube. The time required for the impression material to flow through the tube to the dental tray reduces the available working time of the impression material.

A problem with viscous material extrusion devices is that the working and set times must be monitored by a separate timer or clock. What is needed is a system that incorporates a timer to keep track of the working and set times of the material immediately after the components are mixed. What is also needed is a compact light weight system which can be placed close to the tray so that the viscous material can be delivered to the tray without travelling through a long tube which consumes the working time wastes.

SUMMARY OF THE INVENTION

The present invention is a light weight portable impression material dispensing system used to inject impression material into dental trays to make molds of a patient's mouth. The inventive system utilizes pressurized gas to move one or more pneumatic cylinders which drive two rods into a two cylinder dispenser. Each cylinder of the dispenser contains a different material component. The two material components are mixed and extruded through a tube connected to a dental tray. A timer incorporated into the inventive system monitors the time after the material components have been mixed and inform the operator of the remaining working time and set time of the material. In one embodiment, switches used to control the flow of material are mounted in a hand grip attached to the injection system so that the entire system is held and controlled by one hand. In another embodiment, the system is a table top unit which is also controlled with one hand.

BRIEF DESCRIPTION OF THE DRAWINGS

The invention is herein described, by way of example only, with reference to embodiments of the present invention illustrated in the accompanying drawings, wherein.

DETAILED DESCRIPTION

Figure 1:
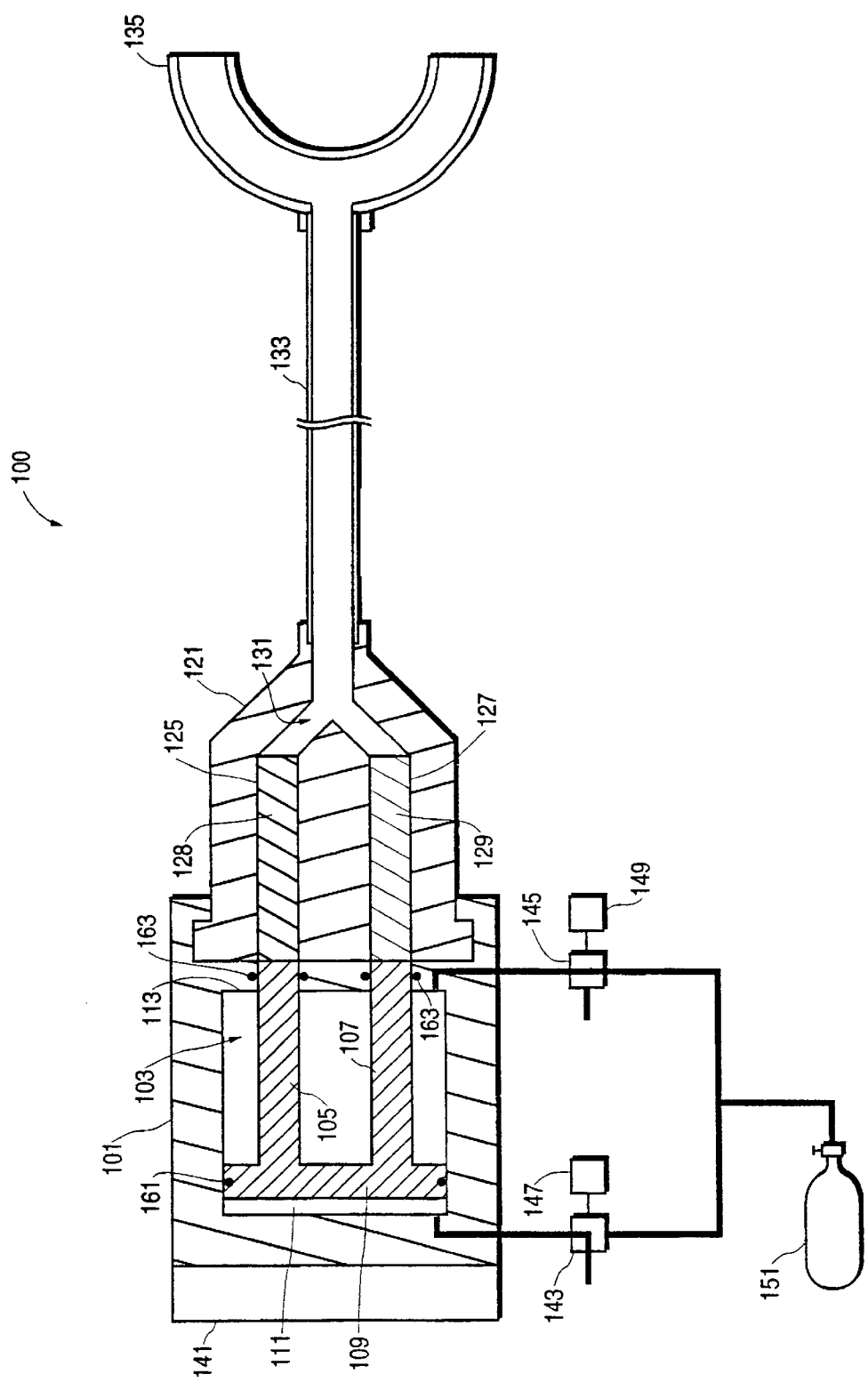
FIG. 1 illustrates a cross section view of the impression material system.

The following is a detailed description of the presently preferred embodiments of the present invention. However, the present invention is in no way intended to be limited to the embodiments discussed below or shown in the drawings. Rather, the description and the drawings are merely illustrative of the presently preferred embodiments of the invention.

Referring to FIG. 1, an embodiment of the present invention is illustrated. The body 101 houses a cylinder 103, a piston 109 and two rods 105, 107. The piston 109 and rods 105, 107 are movable between extended and retracted positions within the cylinder 103 having a front end 113 and a back end 111. In FIG. 1, the system 100 is illustrated with the piston 109 at the back end 111 of cylinder 103 and the ends of rods 105, 107 retracted within the front surface of the body 101. The cylinder 103 may have a circular, rectangular, hexagonal or any other suitable cross section.

With the piston 109 and rods 105, 107 in fully retracted positions, a dispenser 121 having a flanged end 123 can be attached to a grooved fitting at the front surface of the body 101. The dispenser 121 has a first chamber 125 containing a first component 128 of the impression material and a second chamber 127 which contain second component 129 of the impression material. When the flanged end 123 is inserted into the grooved fitting, the first chamber 125 is aligned with rod 105 and the second chamber 127 is aligned with rod 107. The first chamber 125 and second chamber 127 converge at junction 131 which is connected to a tube 133 which is connected to a dental tray 135.

The dispenser 121 is an off the shelf stock item which is typically either a cartridge or pouch configuration. The illustrated embodiments show the cartridge type dispensers 121 which have a flanged end 123 which engages grooves in the body 101, however the inventive system 100 is also compatible other types of material containers. In another embodiment, a pouch containing material 130 or the raw material 130 may be placed in a chamber(s) adjacent to the rods 105, 107. The chamber may be configured such that when the rods 105, 107 enter the chamber(s) the material 130 flows through the tube 133 into the dental tray 135.

The piston 109 and rods 105, 107 are moved within the cylinder 103 by actuating either an extension valve 143 or a retraction valve 145. The extension valve 143 and the retraction valve 145 are three way valves which are connected to a pressurized gas source 151. The actuation valve 143 is connected to the back end 111 of cylinder 103 and the retraction valve 145 is connected to the front end 113 of cylinder 103. In their normal positions, the extension valve 143 and retraction valve 145 block the flow of gas from the pressurized gas source 151 and vent the ends of the cylinder 103 to ambient. In the preferred embodiment, the pressurized gas source 151 is compressed air commonly used in a dental examination room. Other suitable pressurized gas sources 151 include: pressurized nitrogen, air and mixtures of inert gases.

Switches 147, 149 are used to actuate the extension valve 143 and the retraction valve 145, respectively. The connection between the switches 147, 149 and the valves 143, 145 may be: mechanical, electrical, pneumatic or any other suitable interface. In the preferred embodiment, the switches 147, 149 are push buttons mechanically or electrically connected to the extension valve 143 and the retraction valve 145.

The dispenser 121 may only be attached to or removed from the body 101 when the rods 105, 107 are fully retracted. When the retraction valve 145 is actuated, pressurized gas flows from the pressurized gas source 151 into the front end of cylinder 103. The differential pressure across the piston 109 moves it towards the back end 111 of the cylinder 103 retracting the rods 105, 107. Pressure at the back end 111 of the cylinder does not build because the extension valve 143 vents this volume to atmosphere. The piston 109 stops at the end of the cylinder 103 with the ends of the rods 105, 107 fully retracted within the body 101.

The piston 109 fits closely within the cylinder 103. The inner surface of the cylinder 103 may be coated with well known lubricants so that the piston 109 slides smoothly between the front end 113 and the back end 111 of the cylinder 103. In the preferred embodiment, an O-ring 161 may be mounted around the circumference of the piston 109. The O-ring 161 slides against the inner lubricated surface of the cylinder 103 as the piston 109 moves and is compressed between the piston 109 and cylinder 103 forming a gas tight seal which prevents gas from flowing around the piston 109. Because the rods 105, 107 travel through the front end of cylinder 103, similar O-rings 163 may be mounted in the body 101 around the rods 105, 107. The O-rings 161, 163 may be made of rubber, plastic or any other suitable material.

As long as the piston 109 fits closely within the cylinder 103 and the rods 105, 107 fit closely with the body 101 such that a substantial amount of gas does not flow through the cylinder 103, it is not necessary for the system 100 to have O-rings 161, 163. However, the use of O-rings 161, 163 assists in controlling the rate of movement of the piston 109 within the cylinder 103. The piston 109 does not move freely within the cylinder 103 due to the friction caused by the sliding of O-rings 161, 163. More specifically, the rate of movement of the piston 109 through the cylinder 103, will be substantially uniform as long as the differential pressure across the piston 109 is between 25 and 45 psi. Gas pressure into the back end 111 of the cylinder 103 can be regulated by a flow restricting orifice and a pressure relief valve located downstream of the extension valve 143. In the preferred embodiment the pressure relief is set to approximately 45 psi. Although the gas seal mechanisms for the piston 109 and rods 105, 107 have been described as O-rings 161, 163, any other well known and suitable seal may be used including: bellows, lip seals, gaskets, bushings and sleeves.

Figure 2:
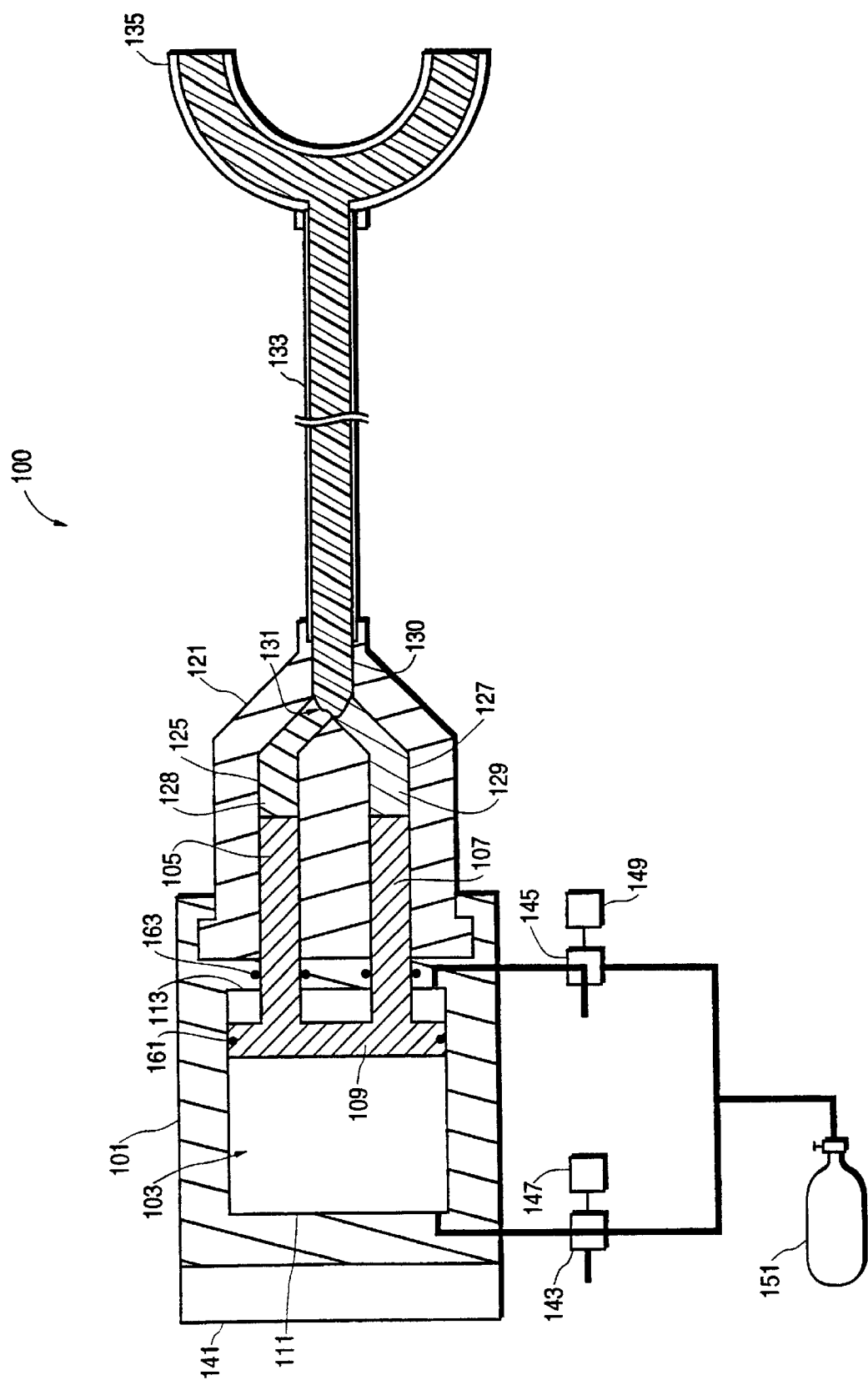
FIG. 2 illustrates a cross section view of the impression material system.

FIG. 2 illustrates the impression material dispensing system 100 in the extended position. To extend the rods 105, 107 into the dispenser 121 the extension valve 143 is actuated pressurized gas flows from the pressurized gas source 151 into the back end 111 of cylinder 103. The differential pressure across the piston 109 moves it towards the front end 113 of cylinder 103 pushing rod 105 into the first chamber 125 and rod 107 into the second chamber 127 of the dispenser 121. The first component 128 in the first chamber 125 and second component 129 in the second chamber 127 are mixed in the junction 131 forming a viscous material 130 which flows through the tube 131 into the dental tray 135 placed within a patient's mouth. When a sufficient amount of viscous material 130 has been injected into the dental tray 135, the operator turns off the extension valve 143 which stops the movement of the piston 109 and the flow of viscous material 130 into the dental tray 135. After the viscous material 130 has been injected into the dental tray 135, the piston 109 and rods 105, 107 are retracted so that the dispenser can be removed and discarded.

Although the viscous material 130 is illustrated as resulting from equal quantities of the first component 128 and the second component 129, it is also contemplated that inventive system 100 may mix the first component and the second component at any other ratio. Specifically, if a larger percentage quantity of the first component 128 is desired, the first chamber 125 can be a wider diameter than the second chamber 127 and the rod 105 can similarly be a wider diameter than the rod 107. By adjusting the cross sectional areas of the first chamber 125 and the second chamber 127, the mix ratio of the first component 128 and the second component 129 can controlled.

As discussed above, the viscous material 130 may have specific working and set times which begin as soon as the first component 128 and second component 129 are mixed. Adjustments can be made to the dental tray 135 before the working time of the impression material 130 has expired but the mold may be damaged by movement of the dental tray 135 after the impression material begins to polymerize or rubberize. When the viscous material 130 has fully hardened and the dental tray 135 is removed from the patient's mouth. The impression of the patient's mouth remains in the hardened impression material 130 forming a mold which may be used to make a replica of the teeth and gums.

A programmable timer 141 having a display may be built into the body 101 which can be programmed with the working time and set time of the impression material 130 being used. After the extension valve 143 is actuated and the viscous material 130 is mixed, the timer 141 is started and the elapsed time is displayed in digital or analog form so that the working and set times can be monitored by the operator. As discussed, the dental tray 135 and viscous material 130 can be moved during the working time, but should not be moved after the working time has elapsed. The dental tray 135 may be removed from the patient's mouth once the viscous material 130 after the set time has elapsed.

In one embodiment, a single button starts both the working and set timers and both the remaining working and set times are displayed. The timer 141 start button may be connected to the extension valve 143, such that when the extension valve 143 is actuated, the timer 141 starts and when the retraction valve 145 is actuated, the timer stops and resets. A speaker may also be connected to the timer 141 so that audible signals may be emitted during the timing process to notify the user of the elapsed time or remaining working and set times.

In another embodiment the timer 141 may have two independent start buttons for the working and set times. Separate timers may be necessary when a substantial amount of time is required to fill the dental tray 135 with viscous material 130. The working timer may be started as soon as the viscous material 130 leaves dispenser 121 so that the adjustments are not made after the initial viscous material 130 enters the dental tray 135 and begins to solidify. However, the set timer may be started later, after the dental tray 135 has been filled with impression material 130 because the dental tray 135 should not be removed until all of the impression material 130 has hardened.

Figure 3:
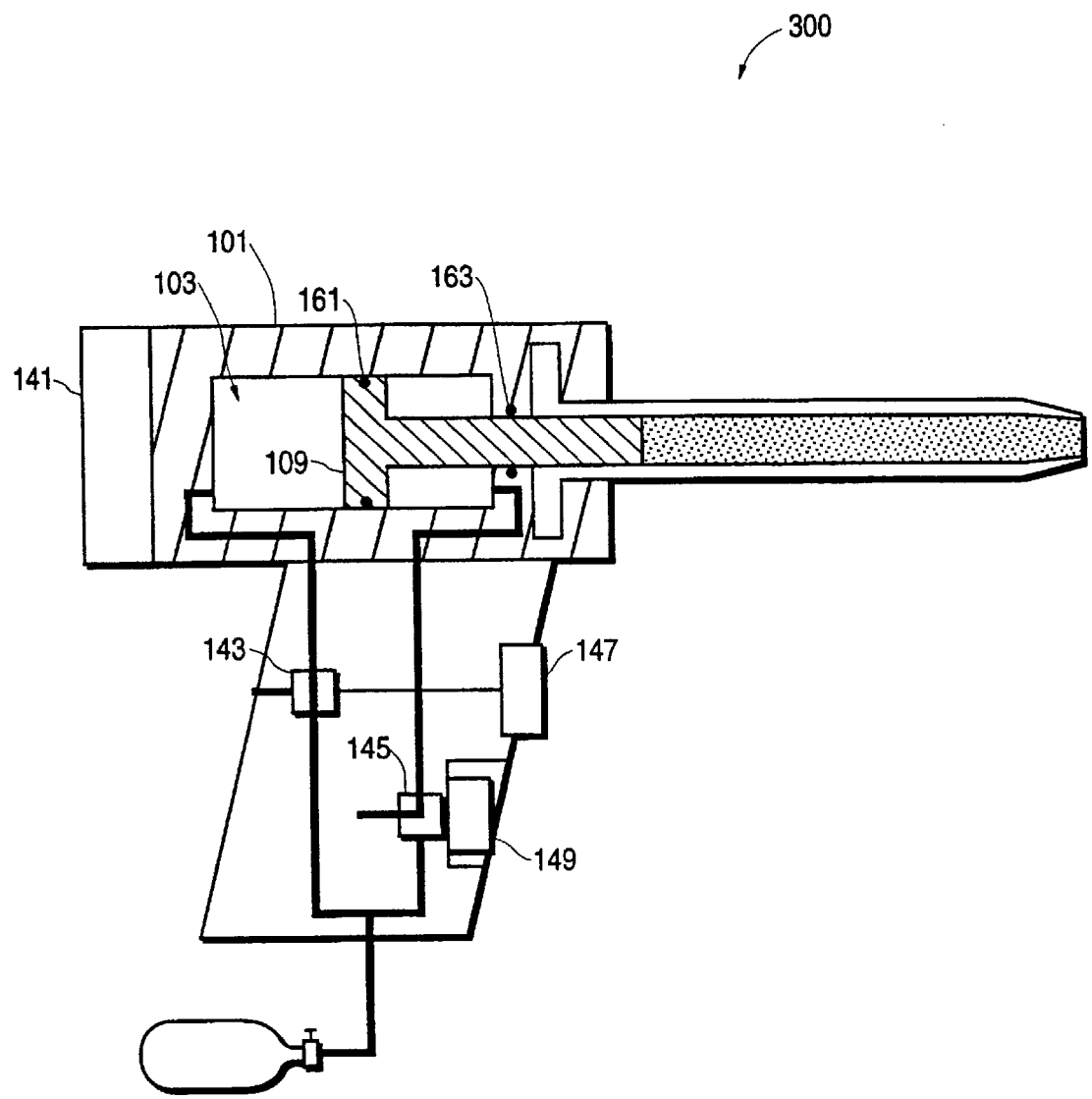
FIG. 3 illustrates an embodiment of the impression material system with a handle.

Referring to FIG. 3, in one embodiment the extension valve 143 and retraction valve 145 is illustrated as being housed in a handle 303 attached to the body 101 which allows the operator to hold the viscous material injection system 300. In this embodiment, extension valve 143 and retraction valve 145 are actuated by switches 147 and 149, respectively, that are built into the handle 203. The switches 147 and 149 are actuated by the operator's grip hand fingers. In this configuration, the impression material injection system is fully operational with one hand and the other hand is free to adjust the dental tray 135 within the patient's mouth. A timer 141 may be mounted on the back of the body 101 allowing the elapsed time to be seen by the operator during viscous material 130 injection.

As discussed above, the retraction valve 145 is typically only utilized to remove or replace dispensers after impression material has been injected into the dental tray in the patient's mouth. Thus, in the preferred embodiment, the switch 149 is recessed in the handle 303 to prevent it from being accidentally pressed and actuating the retraction valve 145.

Figure 4:
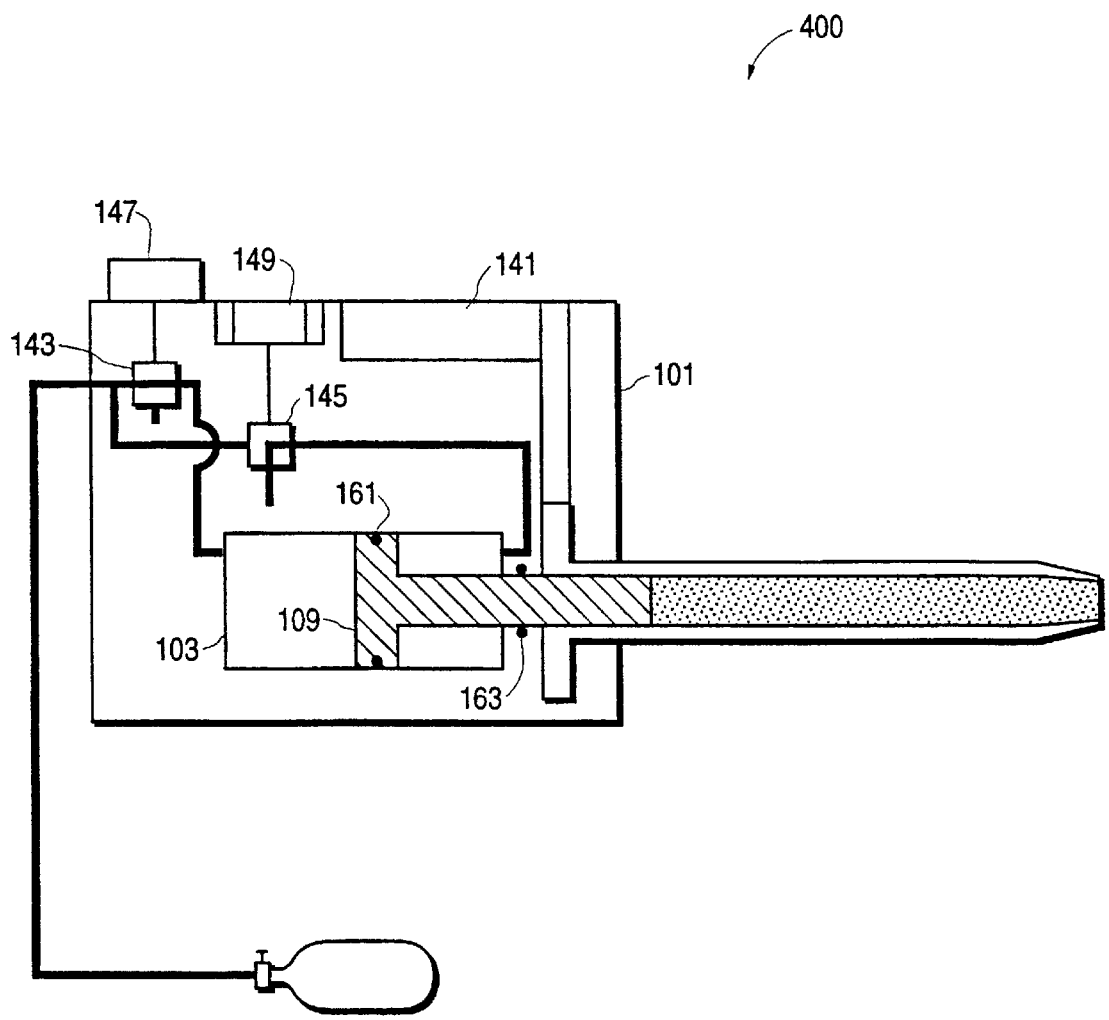
FIG. 4 illustrates another embodiment of the impression material system.

Referring to FIG. 4, a table top embodiment of the impression material injection system 400 is illustrated. In this embodiment, switches 147 and 149 and timer 141 are mounted on top of the body 101. In this embodiment, the impression material injection system is controlled with switches 147 and 149. In another embodiment, the switches 147 and 149 may be mounted on a remote foot pedal allowing actuation of extension valve 143 and retraction valve 145 with the operator's feet. Actuation signals are then sent from the foot pedals to the extension valve 143 and retraction valve 145 via wires, radio signal, pneumatic tubing or any other suitable signal transmission means. Similarly, the timer 141 may be located remotely from the impression material injection system 400.

Switches 147 and 149 may be electrical switches that are used to actuate electrically operated solenoid valves or other electrically actuated valves. It is also contemplated that the switches 147 and 149 may be pneumatic switches connected to actuators mounted on the valves 147 and 149.

As discussed above, the inventive system is used for dentistry and may be exposed to various chemicals commonly found in a dentist's office. To avoid damage due to exposure the external surfaces of the inventive apparatus are made of chemical resistant materials. In the preferred embodiment, the inventive impression material dispensing system is made of injection molded plastic which is not affected by exposure to: formaldehyde, alcohol, glutaraldehyde, fenoliz components, quantiarium ammonia, hydrochloric acid, phenylphenol, chlorophenol as well as any other chemicals used in the medical profession and equipment sterilization processes.

In the foregoing, a viscous material dispensing system has been described as a dental impression material handling system. Although the present invention has been described with reference to specific exemplary embodiments, it will be evident that various modifications and changes may be made to these embodiments without departing from the broader spirit and scope of the invention as set forth in the claims. Specifically, the inventive system may be used for other applications including: mold making, adhesives, epoxies, resins, cement, catalysts, ear, nose and throat medical applications. Accordingly, the specification and drawings are to be regarded in an illustrative rather than a restrictive sense.

What is claimed is:

1. A method of extruding a impression material having a working time and a set time, comprising the steps:

providing an apparatus for extruding the impression material which has a cylinder within a body having a first end and a second end, a piston mounted within the cylinder having at least one rod with a first end attached to the piston and a second end extending through the second end of the cylinder positioned proximate a chamber containing impression material, a first valve in fluid communication with the first end of the cylinder and a pressurized gas source, a programmable unit for measuring the working time or the set time of the impression material; a dental tray and a tube in fluid communication with the dispenser and dental tray;

programming the unit with the working time or the set time of the impression material;

actuating the first valve such that pressurized gas from the pressurized gas source flows into first end of the cylinder moving the piston towards the second end of the cylinder causing the rod to enter the chamber and impression material to be extruded from the chamber through the tube into the dental tray;

starting the unit for visually displaying the working time or the elapsed set time of the impression material; and monitoring the working time or the set time of the impression material.

2. The method of extruding a impression material of claim 1, further comprising:

providing a second valve in fluid communication with the second end of the cylinder and the pressurized gas source;

actuating the second valve such that pressurized gas from the pressurized gas source flows into first end of the cylinder moving the piston towards the second end of the cylinder and causing the rod to retract from the chamber.

3. The method of extruding a impression material of claim 1, further comprising:
providing a hand grip connected to the body and a switch used to activate the first valve mounted on the hand grip;
wherein the first valve is actuated by pressing the switch.

4. The method of extruding a impression material of claim 1 further comprising:
indicating when the working time of the impression material has elapsed.

5. The method of extruding a impression material of claim 1 further comprising:
indicating when the set time of the impression material has elapsed.

6. A method of extruding a impression material having a working time, comprising the steps:
providing an extrusion device having a body, a cylinder having a first cylinder end and a second cylinder end, a piston within the cylinder attached to at least one rod with a first end of the rod is attached to the piston and a second end of the rod extends through the second end of the cylinder and into a chamber containing the impression material having a working time, a first valve in fluid communication with the first end of the cylinder, a pressurized fluid source; a dental tray, a tube in fluid communication with the dispenser and dental tray, and a programmable timer;
programming the timer with the working time of the impression material;
actuating the first valve such that pressurized gas from the pressurized gas source flows into first end of the cylinder moving the piston towards the second end of the cylinder causing the rod to enter the chamber;
extruding impression material from the chamber through the tube into the dental tray; and
starting the programmable unit for visually displaying the elapsed working time of the impression material.

7. The apparatus for extruding a impression material 6, further comprising:
deactivating the first valve to stop the extrusion of the impression material from the chamber.

8. The method of extruding a impression material of claim 6, further comprising the steps:
providing a second valve in fluid communication with the second end of the cylinder and the pressurized gas source;
actuating the second valve such that pressurized gas from the pressurized gas source flows into the second end of the cylinder moving the piston towards the first end of the cylinder and causing the rod to retract from the chamber.

9. The method of extruding a impression material of claim 6 further comprising:
providing a hand grip connected to the body and a switch used to activate the first valve mounted proximate the hand grip.

10. The apparatus for extruding a impression material of claim 9 wherein the switch is mounted on a front surface of the grip.

11. The method of extruding a impression material of claim 6, further comprising:
indicating the remaining working time of the impression material after the start the programmable unit step.

12. The method of extruding a impression material of claim 6, further comprising:
indicating when the working time of the impression material has elapsed.

13. A method of extruding a impression material having a set time, comprising the steps:
providing an extrusion device having a body, a cylinder having a first cylinder end and a second cylinder end, a piston within the cylinder attached to two rods, first ends of the rods are attached to the piston and second ends of the rods extend through the second end of the cylinder positioned, the first rod extends into a first chamber containing a first component of the impression material, the second rod extends into a second chamber containing a second component of the impression material, a first valve in fluid communication with the first end of the cylinder, a pressurized fluid source; a dental tray, a tube in fluid communication with the dispenser and dental tray, and a programmable timer;
programming the timer with the working time of the impression material;
actuating the first valve such that pressurized gas from the pressurized gas source flows into first end of the cylinder moving the piston towards the second end of the cylinder causing the first rod to enter the first chamber and the second rod to enter the second chamber;
mixing the first component of the impression material and the second component of the impression material;
flowing the mixed impression material from the chamber through the tube into the dental tray; and
starting the programmable unit for visually displaying the elapsed working time of the impression material.

14. The method of extruding a impression material of claim 13, further comprising:
deactuating the first valve to stop the flow of pressurized gas from the pressurized gas source into the first end of the cylinder and stop the movement of the piston towards the second end of the cylinder.

15. The method of extruding a impression material of claim 13, further comprising:
providing a second valve in fluid communication with the second end of the cylinder and the pressurized gas source;
actuating the second valve such that pressurized gas from the pressurized gas source flows into second end of the cylinder moving the piston towards the first end of the cylinder and causing the first rod to retract from the first chamber and the second rod to retract from the second chamber.

16. The method of extruding a impression material of claim 13, further comprising:
indicating the remaining working time of the impression material after the start the programmable unit step; and
indicating when the set time of the impression material has elapsed.

17. The method of extruding a impression material of claim 13, further comprising:
programming the timer with the set time of the impression material.

18. The method of extruding a impression material of claim 17, further comprising:
indicating when the set time of the impression material has elapsed.

19. The method of extruding a impression material of claim 13, further comprising:
providing a hand grip connected to the body and a button mounted on a front edge of the hand grip, wherein the button is depressed to actuate the first valve.

20. The method of extruding a impression material of claim 19, further comprising:

provinding a second valve in fluid communication with the second end of the cylinder and the pressurized gas source and a second button mounted on the hand grip;

deactuating the first valve to stop the flow of pressurized gas from the pressurized gas source into the first end of the cylinder and stop the movement of the piston towards the second end of the cylinder; and actuating the second valve by depressing the second button such that pressurized gas from the pressurized gas source flows into second end of the cylinder moving the piston towards the first end of the cylinder and causing the first rod to retract from the first chamber and the second rod to retract from the second chamber.

* * * * *